(12) United States Patent
Park et al.

(10) Patent No.: US 11,399,921 B2
(45) Date of Patent: Aug. 2, 2022

(54) DENTAL FLATTENING DRILL

(71) Applicant: MEGAGEN IMPLANT CO., LTD., Gyeongsan-si (KR)

(72) Inventors: Kwang Bum Park, Daegu (KR); Hyun Wook An, Gyeongsan-si (KR); Jung Ho Nam, Daegu (KR)

(73) Assignee: MEGAGEN IMPLANT CO., LTD.

( * ) Notice: Subject to any disclaimer, the term of this patent is extended or adjusted under 35 U.S.C. 154(b) by 36 days.

(21) Appl. No.: 16/083,481

(22) PCT Filed: Nov. 30, 2016

(86) PCT No.: PCT/KR2016/014000
§ 371 (c)(1),
(2) Date: Sep. 7, 2018

(87) PCT Pub. No.: WO2017/131336
PCT Pub. Date: Aug. 3, 2017

(65) Prior Publication Data
US 2019/0209273 A1    Jul. 11, 2019

(30) Foreign Application Priority Data

Jan. 29, 2016 (KR) .......................... 10-2016-0011097

(51) Int. Cl.
*A61C 8/00* (2006.01)
*B23B 51/08* (2006.01)
(Continued)

(52) U.S. Cl.
CPC .............. *A61C 8/0089* (2013.01); *A61C 1/08* (2013.01); *A61C 3/02* (2013.01); *A61C 8/00* (2013.01); *B23B 51/08* (2013.01)

(58) Field of Classification Search
CPC ....... A61C 8/0089; A61C 8/0092; A61C 3/02; A61C 5/42; B23B 5/108; B23B 5/10;
(Continued)

(56) References Cited

U.S. PATENT DOCUMENTS

| 1,333,388 A | 3/1920 | Chester |
| 2003/0224325 A1* | 12/2003 | Kumar ................. A61C 8/0089 |
| | | 433/163 |

(Continued)

FOREIGN PATENT DOCUMENTS

| CN | 203564352 U | 4/2014 |
| JP | 2001170078 A | 6/2001 |

(Continued)

OTHER PUBLICATIONS

Extended European Search Report for Application No. 16888312.2 dated Jan. 24, 2019.

(Continued)

*Primary Examiner* — Edward Moran
(74) *Attorney, Agent, or Firm* — Renaissance IP Law Group LLP

(57) ABSTRACT

A dental flattening drill is disclosed, which can include a drill lance having a drill blade for forming an implant groove and a drill housing to which the drill lance is detachably coupled. The drill housing includes a processing blade for flattening the alveolar bone region around the implant groove.

6 Claims, 12 Drawing Sheets

(51) Int. Cl.
*A61C 1/08* (2006.01)
*A61C 3/02* (2006.01)

(58) Field of Classification Search
CPC ... B23B 5/08; A61B 17/1637; A61B 17/1695; A61B 17/1673
See application file for complete search history.

(56) References Cited

U.S. PATENT DOCUMENTS

2005/0003327 A1 1/2005 Elian et al.
2015/0305835 A1* 10/2015 Debold .................. A61C 3/02
433/173

FOREIGN PATENT DOCUMENTS

| KR | 100759261 B1 | 9/2007 |
| KR | 101166161 B1 | 7/2012 |
| KR | 101192219 B1 | 10/2012 |
| KR | 20130001046 U | 2/2013 |
| KR | 200467202 Y1 | 6/2013 |
| KR | 20130124833 A | 11/2013 |

OTHER PUBLICATIONS

Extended European Search Report for Application No. 16888312.2 dated Sep. 20, 2019.

* cited by examiner

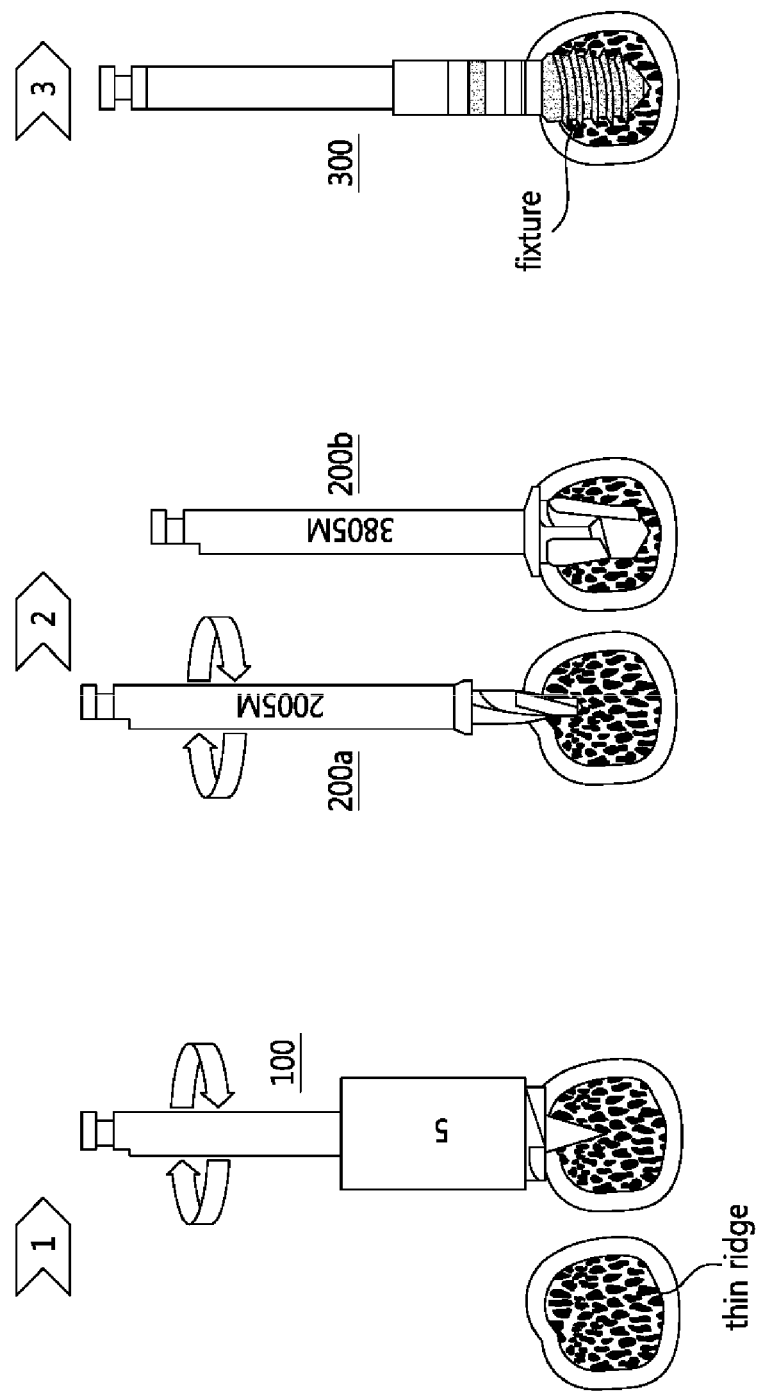

DENTAL FLATTENING DRILL

TECHNICAL FIELD

The inventive concept relates to a dental flattening drill, and more particularly, to a dental flattening drill which may enable easy, accurate, and previous drilling at a position for placing a fixture with respect to an irregular alveolar bone like a thin ridge and flattening an area of an end portion of the alveolar bone so that the fixture can be stably fixed at an accurate position.

BACKGROUND ART

An implant originally means a substitute used to restore lost human tissues. In a dental field, however, the implant refers to a series of procedures to transplant an artificial tooth.

In other words, to replace a lost dental root, the implant is a series of dental procedures to restore a function of a tooth by placing a fixture, which is a dental root formed of titanium and having no rejection to a human body, in an alveolar bone where a tooth is lost, and then fixing an artificial tooth thereto.

In the case of a general prosthesis or denture, surrounding teeth or bones may be damaged as time passes. In contrast, since the implant does not harm the surrounding tooth tissues, provides the same function and shape as a natural tooth, has no tooth decay, the implant may be used semi-permanently.

In an artificial tooth surgery (referred to as an implant surgery), a screw hole is formed by using a drill in an alveolar bone at a position where a fixture is to be placed, the fixture is placed in the screw hole to have osseointegration with the bone forming an artificial dental root, and an abutment is coupled to the fixture and crowned with an artificial tooth that is a final prosthesis.

The implant as above may facilitate restoration of a single missing tooth, enhance the function of a denture for partially toothless and fully toothless patients, improve an aesthetic aspect of dental prosthesis restoration, and furthermore distribute excessive stress applied to surrounding support bone tissues and stabilize a row of teeth.

As described above, in order to place the fixture, a screw hole is formed by punching a hole in the alveolar bone by using a drill.

The drill work is briefly discussed below. The drill work described below is a mere example and there may be a variety of types of drill works.

First, a position where a fixture is to be placed is determined on a surface of the alveolar bon by using a round drill as an initial drill, Next, after cutting and slightly opening an end portion of the alveolar bone where a tooth is lost, a hole of a predetermined depth is punched by mounting a guide drill on a predetermined tool, with water supplied to the alveolar bone.

The hole is enlarged by using a first drill with water supplied to the alveolar bone, and an end portion of the hole is enlarged by using a pilot drill with water supplied to the alveolar bone.

Next, a lower end portion of the hole is enlarged by using a final drill with water supplied to the alveolar bone.

The screw hole for placing a fixture is completed by forming a screw thread in the hole by using a tap drill with water supplied to the alveolar bone.

The above drill work, that is, the forming of a screw hole in the alveolar bone by punching, may be generally applied to patients having a general mouth structure, in particular, having a normal ridge, that is, an end portion of the alveolar bone is large.

However, when the alveolar bone is not general, that is, irregular, for example, the end portion of the alveolar bone is excessively narrow, that is, the alveolar bone forms a thin ridge, the above method may not be employed as it is.

In other words, since the thin ridge has an excessively narrow end portion, the drill work is unavoidably performed on an inclined surface. When the drill work is performed on the inclined surface, the drill work may not be smoothly performed because the drill slips on the inclined surface. Accordingly, it is difficult to form the screw hole in the alveolar bone.

Thus, when the alveolar bone has the thin ridge that is not general and is irregular, a flattening work to make a surface where the fixture is to be placed flat is performed ahead to make a flat surface and the above-described drill work is performed on a flattened surface, thereby forming the screw hole.

As such, the surgery may be made easy and accurate by using a drill suitable for the flattening work to flatten the end portion of the thin ridge.

In other words, there is a demand for development of technologies regarding new dental flattening drills which may enable easy, accurate, and previous drilling at a position for placing a fixture with respect to an irregular alveolar bone like the thin ridge and also flatten an area of the end portion of the alveolar bone.

DETAILED DESCRIPTION OF THE INVENTIVE CONCEPT

Technical Problem

The inventive concept provides a dental flattening drill which may enable easy, accurate, and previous drilling at a position for placing a fixture with respect to an irregular alveolar bone like a thin ridge and flattening an area of an end portion of the alveolar bone so that the fixture can be stably fixed at an accurate position.

Advantageous Effects

According to the present inventive concept, since drilling is easily, accurately, and previously performed at a position for placing a fixture in an irregular alveolar bone like a thin ridge and an area of an end portion of the alveolar bone is flattened, the fixture can be stably fixed at an accurate position.

DESCRIPTION OF THE DRAWINGS

FIG. 12 is an image showing steps of a process of placing a fixture after flattening a thin ridge by using a dental flattening drill, according to an embodiment.

BEST MODE

Figure 1:
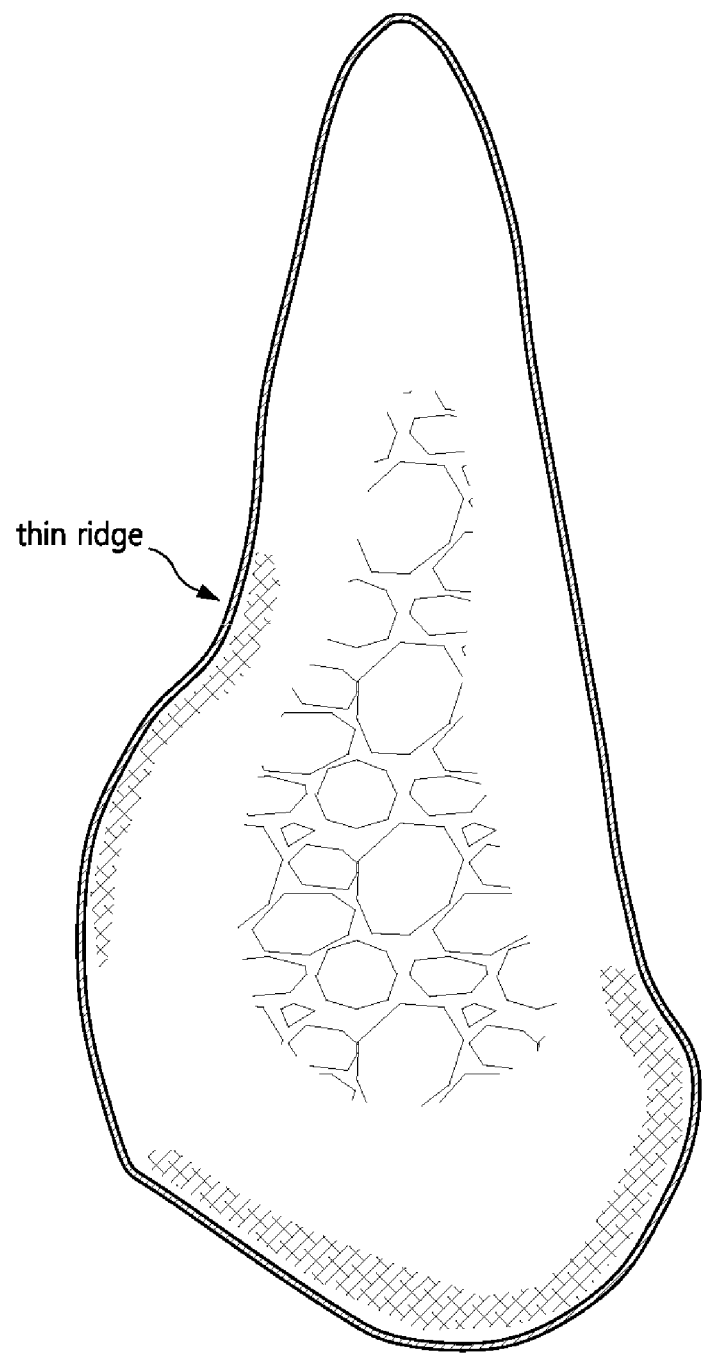
FIG. 1 illustrates a thin ridge alveolar bone.

According to an aspect of the inventive concept, there is provided a dental flattening drill including a drill lance having a drill blade that forms a placement hole by drilling an alveolar bone at a placement position where a fixture is to be placed by a preset depth, and a drill housing, to which the drill lance is detachably coupled, having a processing blade that flattens an area of the alveolar bone around the placement hole.

The drill blade may be arranged radially inside an end mill processing blade of the drill housing.

The drill blade of the drill lance may protrude more than the processing blade of the drill housing in a direction in which the drill lance is coupled to the drill housing.

The drill lance may include a unit shaft having one end portion where the drill blade is formed, and a boss provided on one side of the unit shaft and caught and supported by the drill housing.

The drill blade may be an awl type drill blade having a sharp end portion, the awl type drill blade may have a triangular pyramid shape, and the boss may have a polygonal sectional shape.

The drill lance may further include a cylindrical insertion portion provided on a side surface of the boss toward the drill blade, and a tool mounting portion provided on the other end portion of the unit shaft.

The processing blade may be continuously formed along a circumferential direction of a leading end portion of the drill housing.

The drill housing may have a shape of a hollow pipe through which the drill lance passes.

An alveolar bone crushed powder storing space portion storing alveolar bone crushed powder produced when the alveolar bone is crushed may be provided inside the drill housing.

The processing blade may be an end mill processing blade having blades on a bottom and lateral surfaces. The drill housing may include a housing body having an end portion where the end mill processing blade is formed, a boss catching step, by which the boss of the drill lance is caught and supported, is provided in the housing body, and an insertion hole, into which a cylindrical insertion portion of the drill lance is inserted, is formed inside the boss catching step.

An outer wall of the boss and an inner wall of the housing body contacting each other may have a non-circular shape.

The dental flattening drill may further include a detachable coupling portion provided on the drill lance and the drill housing and detachably coupling the drill lance to the drill housing.

The detachable coupling portion may include a ball plunger provided in any one of the drill lance and the drill housing and including a ball and an elastic member elastically pressing the ball, and a ball accommodation portion provided in the other one of the drill lance and the drill housing and accommodating the ball plunger.

The ball plunger may protrude from an outer wall of one side of the drill lance, and the ball accommodation portion may be concavely formed in an inner wall of the drill housing and provided by a plural number to be regularly arranged in a circumferential direction of the inner wall of the drill housing.

A guide groove guiding the ball of the ball plunger may be further formed in an inner wall of the drill housing where the ball accommodation portion is formed.

The alveolar bone may be a thin ridge having an end portion that is relatively narrow and irregular.

MODE OF THE INVENTIVE CONCEPT

The attached drawings for illustrating exemplary embodiments of the inventive concept are referred to in order to gain a sufficient understanding of the inventive concept and the merits thereof.

Hereinafter, the inventive concept will be described in detail by explaining exemplary embodiments of the inventive concept with reference to the attached drawings. Like reference numerals in the drawings denote like elements.

Figure 2:
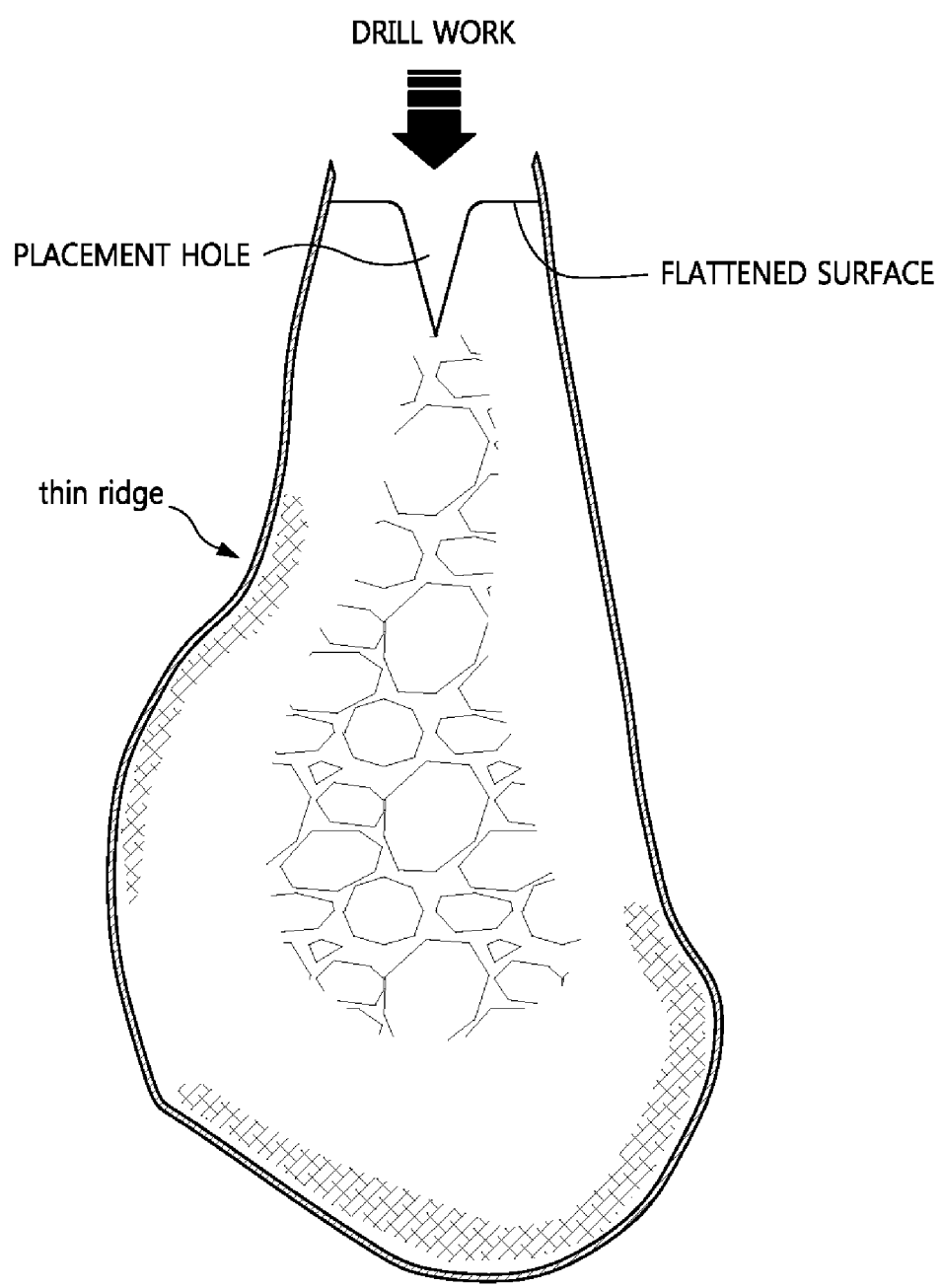
FIG. 2 illustrates the thin ridge alveolar bone of FIG. 1 where a flattening work is performed.
Figure 3:
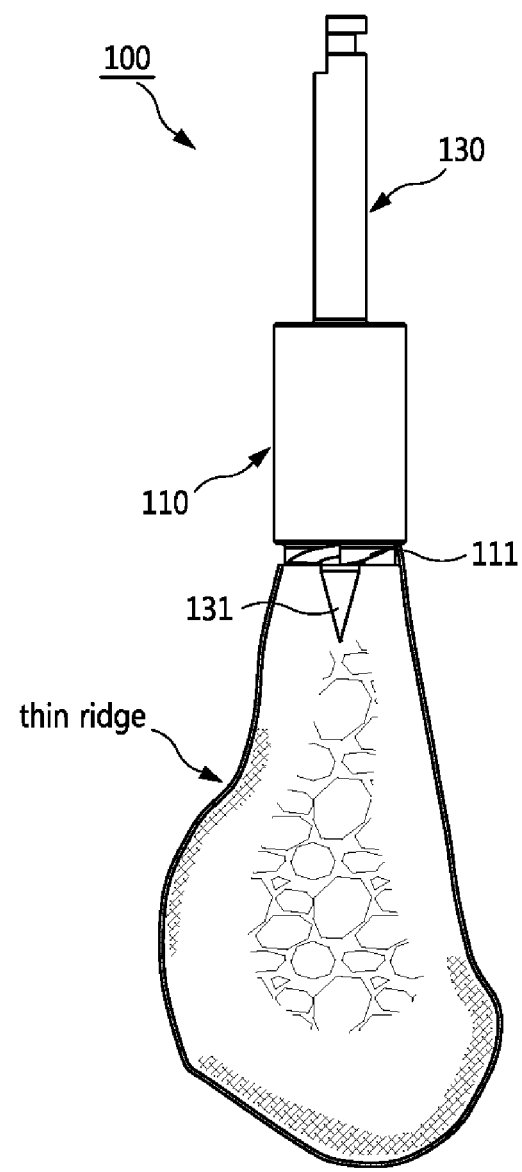
FIG. 3 illustrates a process of performing a flattening work by using a dental flattening drill according to an embodiment.

FIG. 1 illustrates a thin ridge alveolar bone. FIG. 2 illustrates the thin ridge alveolar bone of FIG. 1 where a flattening work is performed. FIG. 3 illustrates a process of performing a flattening work by using a dental flattening drill according to an embodiment.

As described above, in order to place a fixture (see FIG. 12) in an alveolar bone for an implant surgery, the alveolar bone is first punched and a screw hole is formed in a punched hole.

In the case of a general patient having an alveolar bone with a wide end portion (normal ridge), a screw hole (or fixture placement hole) is formed without a preliminary preparation work.

However, when the alveolar bone is not general and is irregular, for example, the end portion of the alveolar bone is excessively narrow and irregular as illustrated in FIGS. 1 and 12, that is, the alveolar bone has a thin ridge, the above method may not be employed as it is.

In this case, as illustrated in FIG. 2, a placement hole is formed by drilling the alveolar bone at a position where the fixture is to be placed by a predetermined depth and a flat surface is formed on an end portion of the thin ridge by flattening the end portion of the thin ridge. By doing so, accurate placement of the fixture as illustrated in FIG. 12 may be possible.

Accordingly, the present embodiment discloses a dental flattening drill 100 having a structure as illustrated in FIGS. 3 to 12 so that the fixture placement position may be easily, accurately, and previously drilled on an irregular alveolar bone having a thin ridge and further an area of the end portion thereof is flattened.

The dental flattening drill 100 according to the present embodiment may be arranged on the end portion of the thin ridge, as illustrated in FIG. 3, and used to form a placement hole and a flattened surface at the end portion of the thin ridge. In particular, in the case of the dental flattening drill 100 according to the present embodiment, since the placement hole and the flattened surface are formed at the end portion of the thin ridge by using a single tool, not separate equipment, efficiency of work may be improved.

Figure 4:
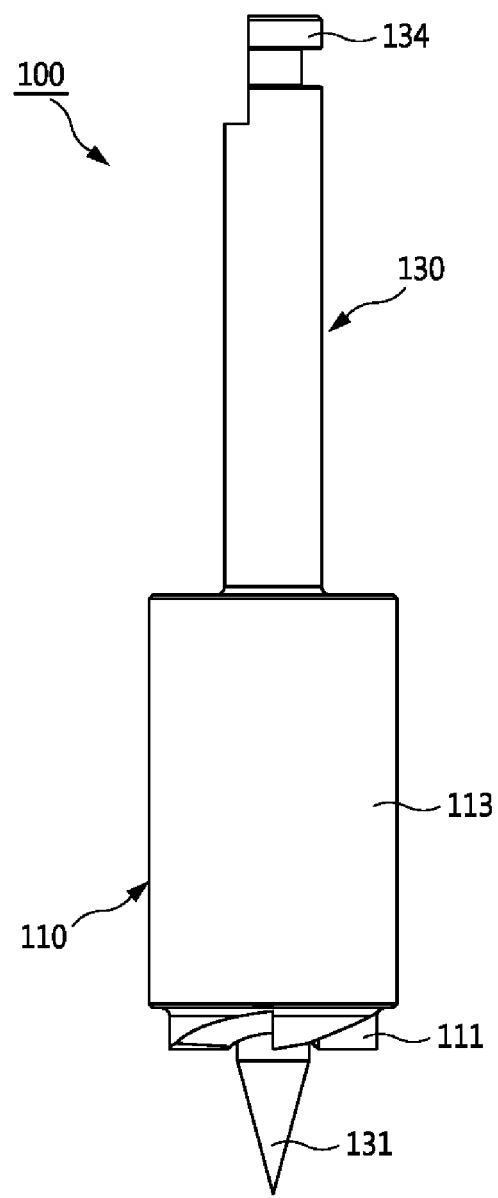
FIG. 4 is an enlarged view of the dental flattening drill of FIG. 3.
Figure 5:
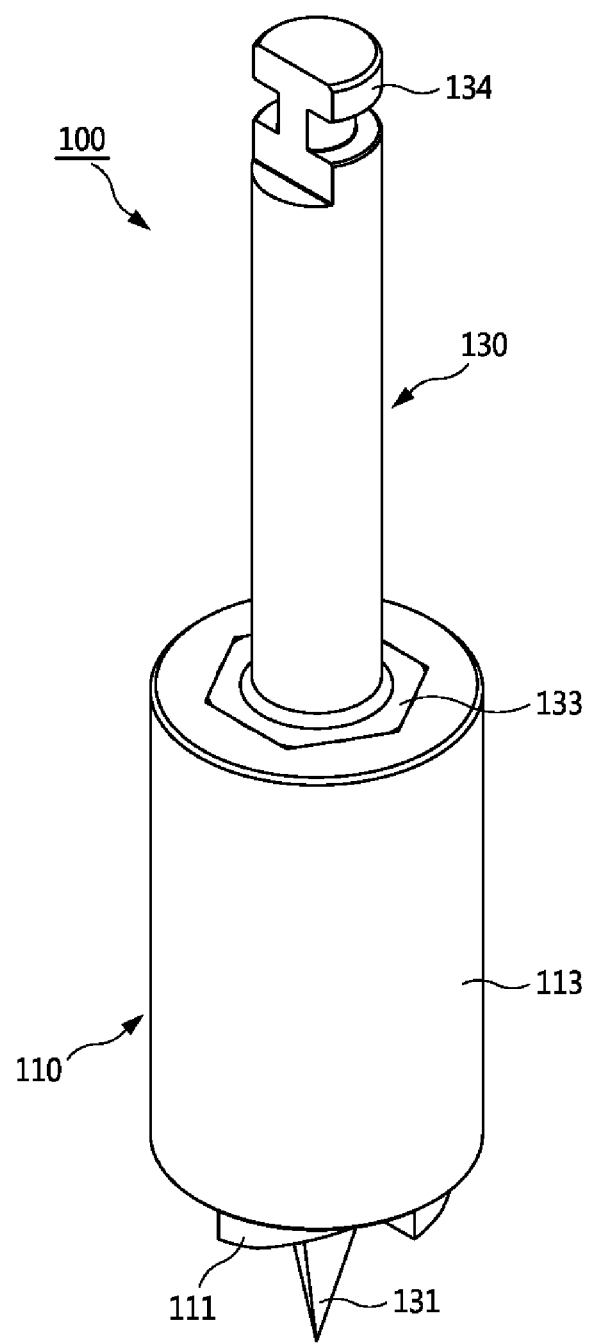
FIGS. 5 and 6 are perspective views of the dental flattening drill viewed at different angles.
Figure 6:
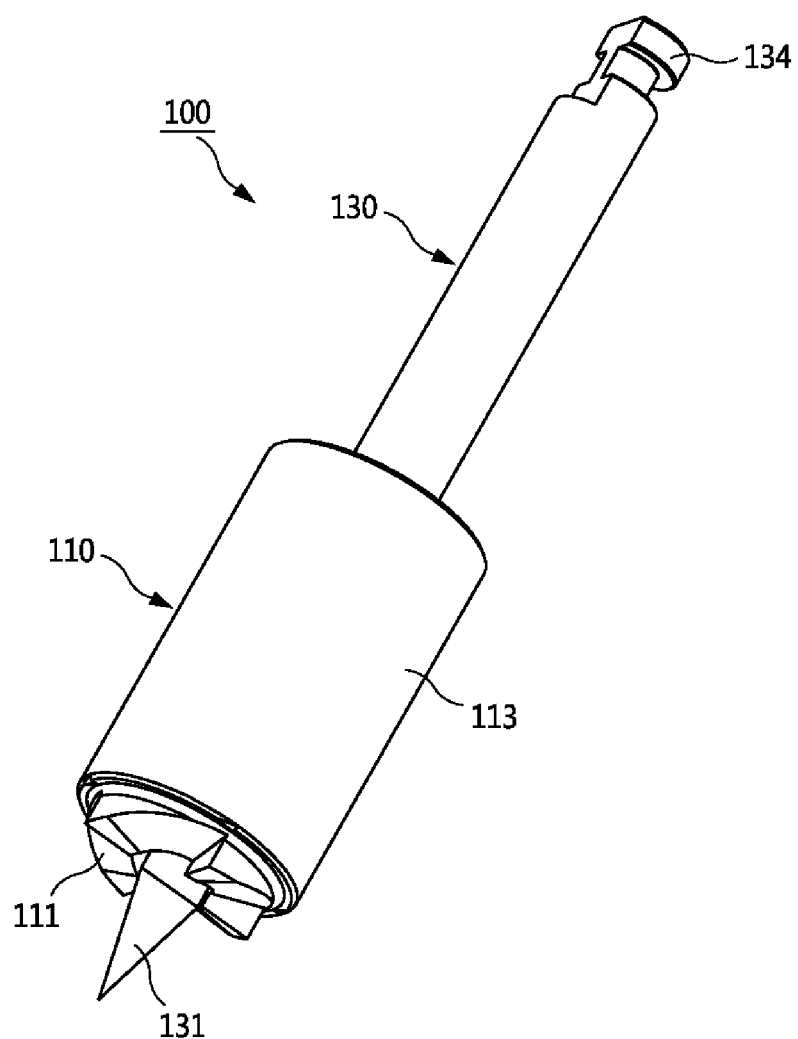
Figure 7:
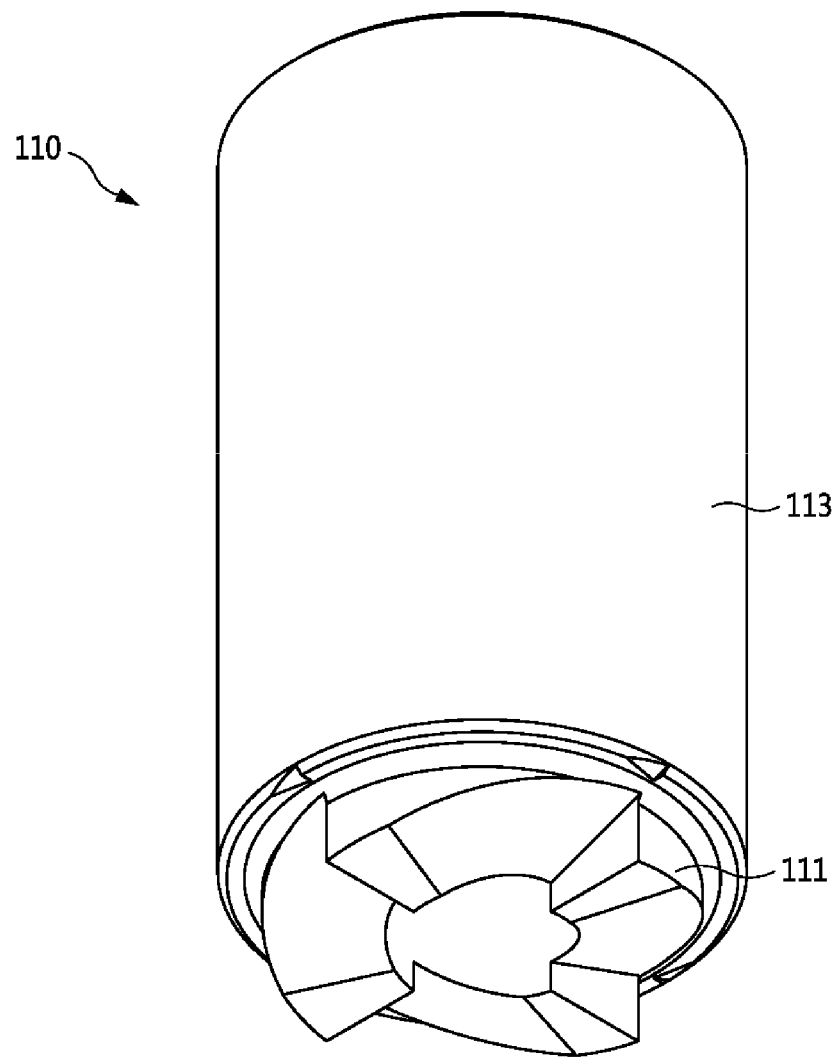
FIGS. 7 and 8 are perspective views of a drill housing viewed at different angles.
Figure 8:
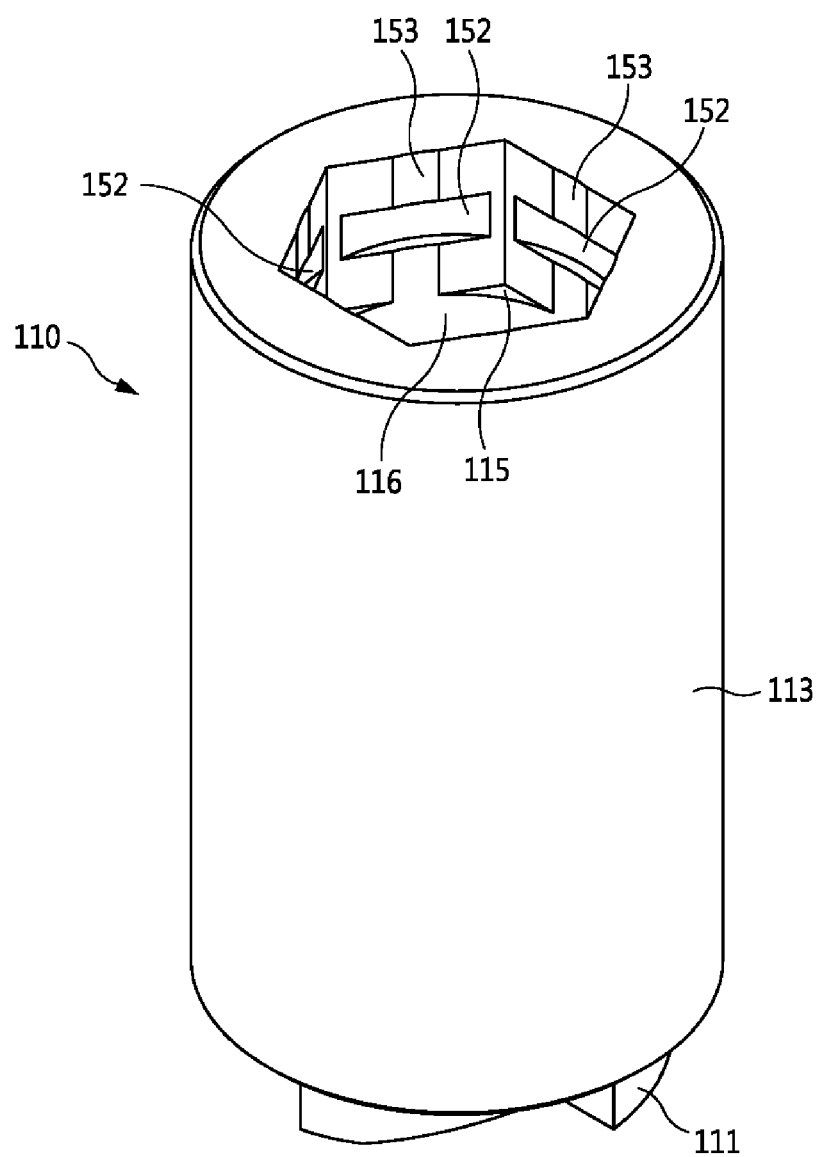
Figure 9:
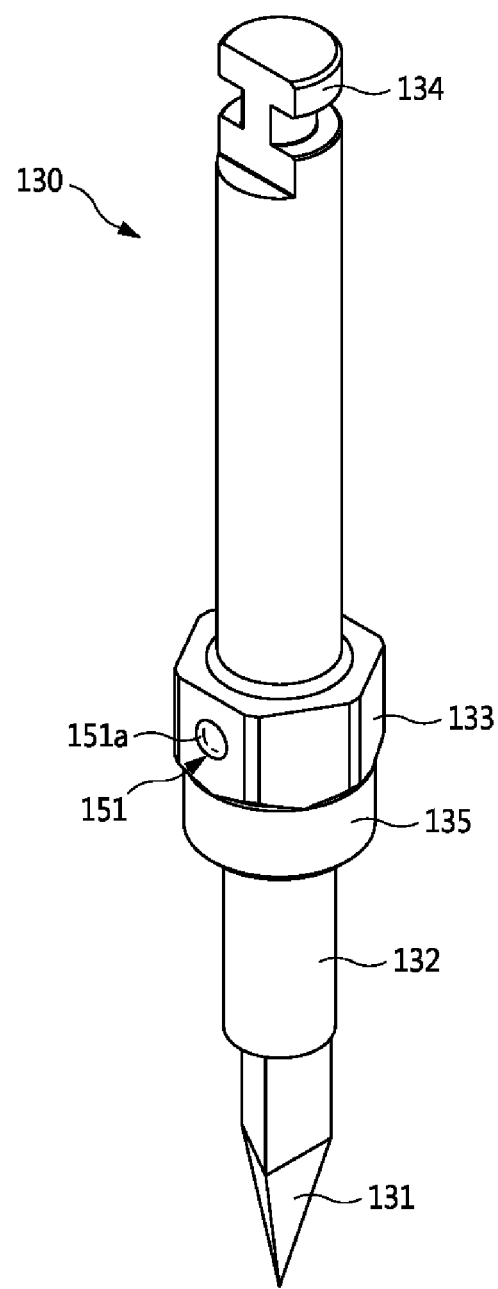
FIGS. 9 and 10 are perspective views of a drill lance viewed at different angles.
Figure 10:
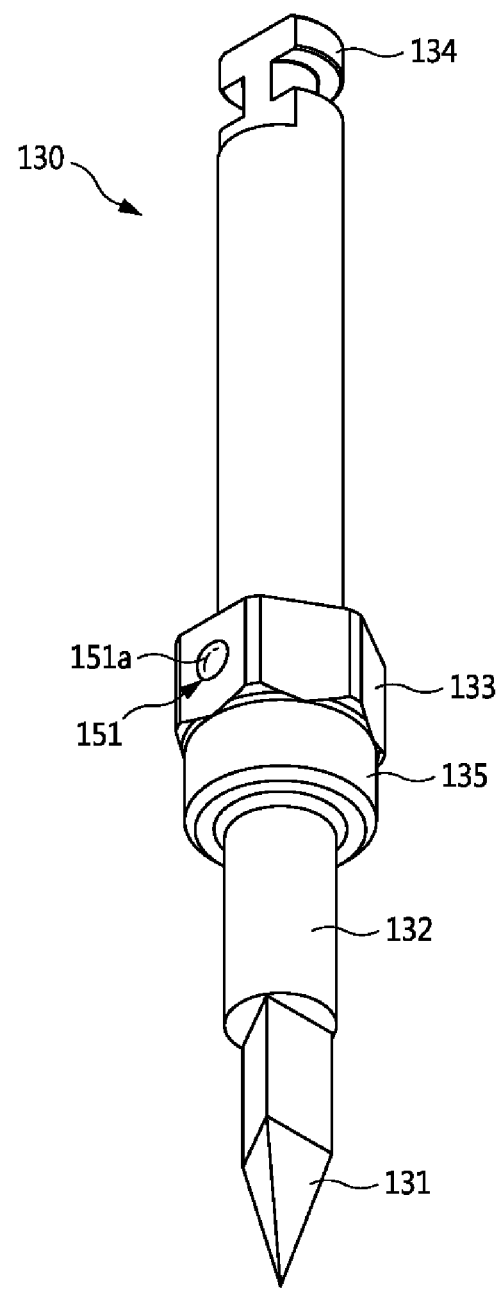
Figure 11:
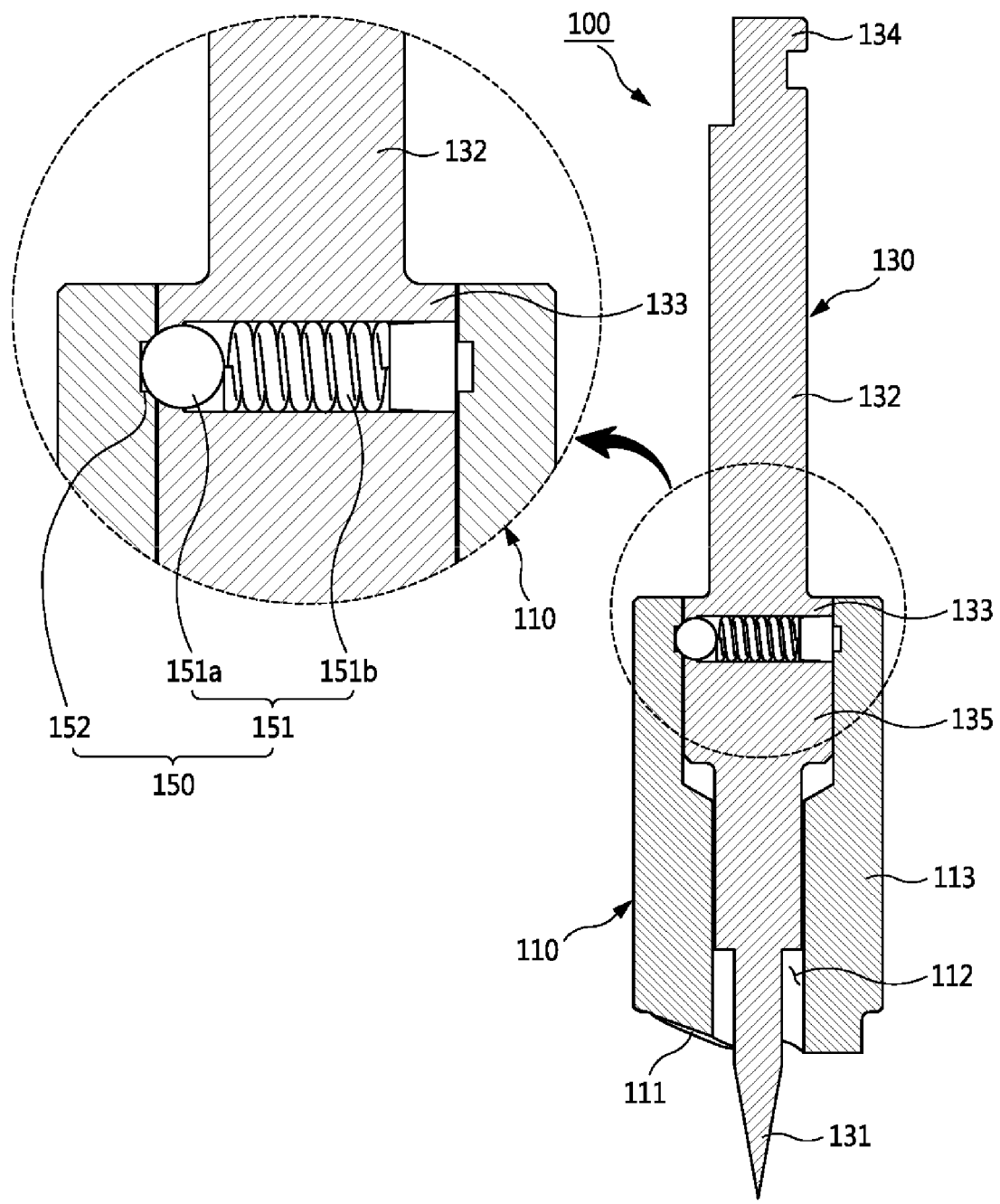
FIG. 11 is a vertical sectional view of FIG. 4.

FIG. 4 is an enlarged view of the dental flattening drill of FIG. 3. FIGS. 5 and 6 are perspective views of the dental flattening drill viewed at different angles. FIGS. 7 and 8 are perspective views of a drill housing viewed at different angles. FIGS. 9 and 10 are perspective views of a drill lance viewed at different angles. FIG. 11 is a vertical sectional view of FIG. 4. FIG. 12 is an image showing steps of a process of placing a fixture after flattening a thin ridge by using a dental flattening drill, according to an embodiment.

Referring to FIGS. 4 to 12, the dental flattening drill 100 according to the present embodiment may enable easy, accurate, and previous drilling at a position for placing a fixture with respect to an irregular alveolar bone like a thin ridge and flattening an area of an end portion of the alveolar bone, and may include two parts, that is, a drill lance 130 and a drill housing 110, which are disassembled from and assembled to each other.

The drill lance 130 and the drill housing 110 may be assembled to each other and used as illustrated in FIG. 3 and may be disassembled from each other for cleaning the inside or for maintenance or repair. In other words, the drill lance 130 and the drill housing 110 assembled to each other may be arranged at the end portion of the thin ridge, as illustrated in FIG. 3, to perform a drill work by being rotated by a separate drill driving equipment (not shown).

First, the drill lance 130 drills the alveolar bone at a placement position where the fixture is to be placed by a predetermined depth, thereby forming the placement hole.

The drill lance 130 maybe coupled to the drill housing 110 and rotated with the drill housing 110.

The drill lance 130 may include a unit shaft 132 and a boss 133 provided at one side of the unit shaft 132 and caught and supported by a boss catching step 115.

The unit shaft 132 is a long rod type structure, and a drill blade 131, that is, an awl type drill blade 131 having a sharp tip end is provided at one end portion of the unit shaft 132. In other words, the awl type drill blade 131 having a sharp end portion is provided so that a placement hole may be formed at a thin ridge by using the drill lance 130 as illustrated in FIGS. 2 and 3.

As the awl type drill blade 131 is rotated by being arranged at the thin ridge, a placement hole having a shape as illustrated in FIGS. 2 and 3 may be formed in the thin ridge.

In the present embodiment, the awl type drill blade 131 may be manufactured in a triangular pyramid shape. The awl type drill blade 131 provided on the drill lance 130 may be arranged radially inside an end mill processing blade 111 of the drill housing 110 that is described later.

In addition, the awl type drill blade 131 of the drill lance 130 may protrude more than the end mill processing blade 111 of the drill housing 110 in a direction in which the drill lance 130 is coupled to the drill housing 110. Accordingly, the placement hole may be formed aside from a flattened surface.

A tool mounting portion 134 is provided at the other end portion of the unit shaft 132. The tool mounting portion 134 may be a place to be used for mounting the dental flattening drill 100 according to the present embodiment on the separate drill driving equipment.

The boss 133 is caught and supported by the boss catching step 115 of the drill housing 110. The drill lance 130 may be inserted into the drill housing 110 until the boss 133 is caught and supported by the boss catching step 115.

In this state, an outer wall of the boss 133 and an inner wall of a housing body 113 contacting each other may have a non-circular shape so that the drill lance 130 is not freely rotated in the drill housing 110.

In the present embodiment, the boss 133 has a shape like a hexagonal nut, and an inner wall of the housing body 113 is manufactured to have six faces corresponding to the hexagonal nut. Accordingly, when the boss 133 is inserted into the inner wall of the housing body 113, the boss 133 may not be freely rotated.

Also, since the boss 133 does not necessarily have the shape like the hexagonal nut, the right scope of the present inventive concept may not be limited to the shape presented on the drawings.

A cylindrical insertion portion 135 may be provided on a side surface of the boss 133 toward the awl type drill blade 131. When the drill lance 130 is coupled to the drill housing 110, the cylindrical insertion portion 135 is inserted into an insertion hole 116 (see FIG. 8) of the drill housing 110 so that a coupling force between the drill lance 130 and the drill housing 110 may be improved.

Next, the drill housing 110 is a cylindrical structure to which the drill lance 130 is detachably coupled, and flattens an upper portion of the alveolar bone around the placement hole at the thin ridge as illustrated in FIG. 2, thereby forming a flattened surface.

A processing blade, that is, the end mill processing blade 111 having blades on a bottom and lateral surfaces thereof, is formed on an end portion of the drill housing 110 to flatten the upper portion of the alveolar bone around the placement hole.

As described above, the end mill processing blade 111 may be arranged radially outside the awl type drill blade 131 provided on the drill lance 130, forming the flattened surface on the thin ridge at its position.

As illustrated in FIG. 11, since the drill lance 130 is coupled (assembled) to the drill housing 110 by being partially inserted into the drill housing 110, the drill housing 110 may have a hollow pipe shape so that the drill lance 130 may pass therethrough.

The drill housing 110 may include the housing body 113 as a cylindrical structure. The end mill processing blade 111 for a flattening work of the thin ridge is formed on a leading end portion of the housing body 113 that is a hollow pipe structure.

In particular, the end mill processing blade 111 also has a function of keeping a position of the awl type drill blade 131 provided on the drill lance 130 not to escape from the position when the awl type drill blade 131 is shaken during rotation. The end mill processing blade 111 rotates together with the awl type drill blade 131 and performs a flattening work on the upper portion of the thin ridge.

The end mill processing blade 111 may be continuously formed in a circumferential direction on a leading end portion of the drill housing 110. Accordingly, shaking during the thin ridge flattening work decreases so that the flattening work may be stably performed.

An alveolar bone crushed powder storing space portion 112 (see FIG. 11) for storing crushed powder of the alveolar bone produced when the alveolar bone is crushed is provided inside the housing body 113.

In other words, when the flattening work is performed on the alveolar bone as illustrated in FIG. 3, the alveolar bone is crushed and crushed powder or some clods of the alveolar bone may be gathered inside the housing body 113, that is, a space between the drill lance 130 and the hosing body 113. The alveolar bone crushed powder gathered as above may be used during guide bone regeneration (GBR). In this state, the alveolar bone crushed powder stored in the above space may be collected by separating the drill lance 130 and the drill housing 110.

For reference, GBR refers to a surgery performed to promote bone formation using a shield film when no sufficient amount of alveolar bone exists around a placed fixture or the alveolar bone is insufficient at a place where the fixture is to be placed. In this state, it is known that, when a patient's own bone is used, the surgery may be more easily performed.

A ball accommodation portion 152 that is a constituent element of a detachable coupling portion 150 is provided on an upper end portion of the inner wall of the housing body 113, which is described later.

The boss catching step 115 is provided on the upper end portion of the inner wall of the housing body 113, forming a place where the boss 133 of the drill lance 130 is caught and supported. In other words, when the drill lance 130 is inserted into the drill housing 110 to couple or assemble the drill lance 130 to the drill housing 110, the drill lance 130 may be inserted into the drill housing 110 only to the boss catching step 115 where the boss 133 of the drill lance 130 is caught and supported. In this state, the drill lance 130 may be coupled or assembled to the drill housing 110.

The dental flattening drill 100 according to the present embodiment may further include the detachable coupling portion 150 to allow the drill lance 130 to be detachably coupled to the drill housing 110.

In other words, the detachable coupling portion 150 is provided between the drill lance 130 and the drill housing 110 and detachably coupling the drill lance 130 to the drill housing 110. Since the detachable coupling portion 150 is provided between the drill lance 130 and the drill housing 110 so that the drill lance 130 and the drill housing 110 are detachably coupled to each other, several drill housing (not shown) having different diameters may be commonly used with respect to one drill lance.

Accordingly, the dental flattening drill according to the present embodiment may be easily applied to patients having different thin ridge areas. In addition, since a drill housing having a relatively small diameter is first used and then a drill housing having a relatively large diameter may be used, a flattening work may be easily performed.

The detachable coupling portion 150 applied to the dental flattening drill 100 of the present embodiment is provided in the boss 133 of the drill lance 130 and the housing body 113 of the drill housing 110. However, the detachable coupling portion 150 may be provided at a different position, regardless of positions.

The detachable coupling portion 150 may include a ball plunger 151 provided on any one of the boss 133 of the drill lance 130 and the housing body 113 of the drill housing 110 and the ball accommodation portion 152 provided on the other one of the boss 133 of the drill lance 130 and the housing body 113 of the drill housing 110 and accommodating the ball plunger 151.

In the present embodiment, the ball plunger 151 protrudes from an outer wall of the boss 133 of the drill lance 130, whereas the ball accommodation portion 152 is concavely formed in the inner wall of the housing body 113 of the drill housing 110.

However, the opposite case is available. In other words, the ball plunger 151 may protrude from the inner wall of the housing body 113 of the drill housing 110, whereas the ball accommodation portion 152 may be concavely formed in the outer wall of the boss 133 of the drill lance 130.

In this case, it is sufficient that both the ball plunger 151 and the ball accommodation portion 152 is provided by one. However, in the present embodiment, the ball accommodation portion 152 may be provided by a plural number and arranged regularly along a circumferential direction of the inner wall of the housing body 113 of the drill housing 110.

When the ball accommodation portion 152 is provide by a plural number as in the present embodiment, a coupling or assembling work between the drill lance 130 and the drill housing 110 may be made easy.

The ball plunger 151 may include a ball 151a that may be selectively inserted into the ball accommodation portion 152 and an elastic member 151b contacting the ball 151a and elastically pressing the ball 151a in a direction in which the ball 151a is inserted into the ball accommodation portion 152.

A guide groove 153 for guiding the ball plunger 151 is formed in the inner wall of the drill housing 110 where the ball accommodation portion 152 is formed. Accordingly, when the drill lance 130 and the drill housing 110 are coupled to each other, the ball plunger 151 is guide along the guide groove 153 and then accommodated in the ball accommodation portion 152. Accordingly, a coupling work between the drill lance 130 and the drill housing 110 may be performed very smoothly.

A series of processes to place the fixture by using the dental flattening drill 100 according to the present embodiment is described below with reference to FIGS. 3 and 12.

First, the drill lance 130 and the drill housing 110 are assembled to each other by using the detachable coupling portion 150 and arranged at an end portion of a thin ridge and rotated as illustrated in FIG. 3 and FIG. 12 (1).

Then, a placement hole and a flattened surface are respectively formed by the awl type drill blade 131 of the drill lance 130 and the end mill processing blade 111 of the drill housing 110, in an upper end of the thin ridge. In this state, as illustrated in FIG. 12 (2), when final drills 200a and 200b to use are, for example, Ø2.0-Ø4.3 drills, the drill housing 110 having a diameter (Ø) of 5 mm may be used. As illustrated in FIG. 12 (2), when the final drills 200a and 200b to use are, for example, Ø4.8-Ø5.4 drills, the drill housing 110 having a diameter (Ø) of 6 mm may be used. The above figures are merely for reference and the present disclosure is not limited thereto.

When the placement hole and the flattened surface are formed on the upper end of the thin ridge by using the dental flattening drill 100 according to the present embodiment, the hole where the fixture is to be placed is processed further deeper by sequentially using the final drills 200a and 200b as illustrated in FIG. 12 (2).

Then, as illustrated in FIG. 12 (3), the fixture is placed at its position and fixed thereto by using separate equipment (Handpiece & Ratchet Connector).

As described above, according to the dental flattening drill according to the present inventive concept configured as above, since drilling is easily, accurately, and previously performed at a position for placing a fixture in an irregular alveolar bone like a thin ridge and an area of an end portion of the alveolar bone is flattened, the fixture can be stably fixed at an accurate position.

While the inventive concept has been particularly shown and described with reference to exemplary embodiments thereof, it will be understood that various changes in form and details may be made therein without departing from the spirit and scope of the following claims.

INDUSTRIAL APPLICABILITY

The present invention can be used in dental treatment for implant surgery.

The invention claimed is:

1. A dental flattening drill comprising:
a drill lance comprising a drill blade configured to form a placement hole by drilling an alveolar bone at a placement position where a fixture is to be placed by a preset depth; and
a drill housing, to which the drill lance is detachably coupled, comprising a processing blade configured to flatten an area of the alveolar bone around the placement hole,
wherein the drill housing comprises a housing body having an end portion where the processing blade is formed,
wherein the housing body and processing blade are spaced apart from the drill blade to define an alveolar bone crushed powder storing space portion configured to receive crushed alveolar bone;
wherein the drill blade and the processing blade are the only blades of the dental flattening drill and the drill blade is arranged radially inside the processing blade of the drill housing,
wherein the drill blade of the drill lance protrudes more than the processing blade of the drill housing in a direction in which the drill lance is coupled to the drill housing,
wherein the drill lance comprises:
a unit shaft having one end portion where the drill blade is formed,
a boss provided on one side of the unit shaft and caught and supported by the drill housing,
a cylindrical insertion portion provided on a side surface of the boss toward the drill blade, and
a tool mounting portion provided on the other end portion of the unit shaft, and
wherein the processing blade is an end mill processing blade having blades on a bottom and lateral surfaces,
a boss catching step, by which the boss of the drill lance is caught and supported, is provided in the housing body, and
an insertion hole, into which the cylindrical insertion portion of the drill lance is inserted, is formed inside the boss catching step;
wherein the drill lance is detachably coupled to the drill housing and comprises:
a detachable coupling portion provided on the drill lance and the drill housing and detachably coupling the drill lance to the drill housing, wherein the detachable coupling portion comprises:
a ball plunger provided in any one of the drill lance and the drill housing and comprising a ball and an elastic member elastically pressing the ball; and
a ball accommodation portion provided in the other one of the drill lance and the drill housing and accommodating the ball plunger,
wherein a guide groove guiding the ball of the ball plunger is formed in an inner wall of the drill housing where the ball accommodation portion is formed.

2. The dental flattening drill of claim 1, wherein the drill blade is an awl type drill blade having a sharp end portion, the awl type drill blade has a triangular pyramid shape, and the boss has a polygonal sectional shape.

3. The dental flattening drill of claim 1, wherein the processing blade is continuously formed along a circumferential direction of a leading end portion of the drill housing.

4. The dental flattening drill of claim 1, wherein the drill housing has a shape of a hollow pipe through which the drill lance passes.

5. The dental flattening drill of claim 1, wherein an outer wall of the boss and an inner wall of the housing body contacting each other have a non-circular shape.

6. The dental flattening drill of claim 1, wherein the ball plunger protrudes from an outer wall of one side of the drill lance, wherein the dental flattening drill comprises a plurality of the ball accommodation portions regularly arranged in a circumferential direction of the inner wall of the drill housing, and wherein each of the ball accommodation portions is concavely formed in an inner wall of the drill housing.

* * * * *